United States Patent [19]

Church et al.

[11] Patent Number: 5,279,816
[45] Date of Patent: Jan. 18, 1994

[54] ORAL COMPOSITION HAVING IMPROVED TOOTH WHITENING EFFECT

[75] Inventors: John A. Church, Princeton Junction; Michael Prencipe, East Windsor, both of N.J.; Menachem Lewin, Jerusalem, Israel

[73] Assignee: Colgate-Palmolive Co., New York, N.Y.

[21] Appl. No.: 796,160

[22] Filed: Nov. 22, 1991

[51] Int. Cl.$^5$ .......................... A61K 7/16; A61K 7/20
[52] U.S. Cl. ......................................... 424/53; 424/49
[58] Field of Search ............................................ 424/53

[56] References Cited

U.S. PATENT DOCUMENTS

| | | |
|---|---|---|
| 3,988,433 | 10/1976 | Benedict ................................ 424/53 |
| 4,670,252 | 6/1987 | Sampathkumar ...................... 424/53 |
| 4,716,035 | 12/1987 | Sampathkumar ...................... 424/52 |
| 4,804,530 | 2/1989 | Sampathkumar ...................... 424/53 |
| 4,886,658 | 12/1989 | Charbonneau et al. ............... 424/53 |
| 4,976,955 | 12/1990 | Libin ..................................... 424/53 |
| 4,990,329 | 2/1991 | Sampathkumar ...................... 424/53 |
| 5,000,942 | 3/1991 | Libin ..................................... 424/53 |
| 5,015,408 | 5/1991 | Reuss .................................... 424/53 |
| 5,028,414 | 7/1991 | Sampathkumar ...................... 424/53 |
| 5,055,305 | 10/1991 | Young ................................... 424/53 |
| 5,110,583 | 5/1992 | Sampathkumar ...................... 424/53 |

FOREIGN PATENT DOCUMENTS

| | | |
|---|---|---|
| 123525 | 10/1984 | European Pat. Off. ............. 424/53 |
| 408131 | 1/1991 | European Pat. Off. ............. 424/53 |
| 424020 | 4/1991 | European Pat. Off. ............. 424/53 |
| 1477691 | 6/1977 | United Kingdom ................. 424/53 |
| 1600106 | 10/1981 | United Kingdom ................. 424/53 |
| 2175805 | 12/1986 | United Kingdom ................. 424/53 |

*Primary Examiner*—Shep K. Rose
*Attorney, Agent, or Firm*—Paul Shapiro; Robert C. Sullivan

[57] ABSTRACT

An oral composition effective in whitening teeth comprising an amount of peroxyacetic acid effective to effect improved whitening of teeth.

8 Claims, No Drawings

ORAL COMPOSITION HAVING IMPROVED TOOTH WHITENING EFFECT

BACKGROUND OF THE INVENTION

1. Field of the Invention

This invention relates generally to an oral composition which when applied onto the surface of teeth acts to whiten teeth and more particularly to an oral composition for whitening teeth that is more effective than existing products available to the consumer.

2. The Prior Art

A tooth is comprised of an inner dentin layer and an outer hard enamel layer that is the protective layer of the tooth. The enamel layer of a tooth is naturally an opaque white or slightly off-white color. It is this enamel layer that can become stained or discolored. The enamel layer of a tooth is composed of hydroxyapatite mineral crystals that create a somewhat porous surface. It is believed that this porous nature of the enamel layer is what allows staining agents and discoloring substances to permeate the enamel and discolor the tooth.

Many substances that a person confronts or comes in contact with on a daily basis can "stain" or reduce the "whiteness" of one's teeth. In particular, the foods, tobacco products and fluids such as tea and coffee that one consumes tend to stain one's teeth. These products or substances tend to accumulate on the enamel layer of the tooth and form a pellicle film over the teeth. These staining and discoloring substances can then permeate the enamel layer.

This problem occurs gradually over many years, but imparts a noticeable discoloration of the enamel of one's teeth.

One method for whitening teeth used by dental professionals involves the use of 30% hydrogen peroxide in combination with heat and light to promote the oxidation reaction. This method, although fast, is losing favor with dentists because clinical and scientific evidence shows that an effective whitening process without heat and light is desired.

Another professional method for bleaching teeth involves the use of hydrogen peroxide generating compounds such as urea peroxide (carbamide peroxide) at concentrations of 10% to achieve the desired whitening effect. Urea peroxide rapidly breaks down into hydrogen peroxide due to the water present in saliva. This method is known as an office-monitored at-home bleaching system and involves the use of a mouth guard or tray within which the bleaching agent is placed. The tray is then placed upon the teeth of the patient and bleaching is allowed to take place. This method of treatment has drawbacks including tooth sensitivity, possibly due to demineralization and irritation of oral tissues. An additional disadvantage of the tray application method is that the bleaching effect is very slow.

There is a demand in the marketplace for a tooth whitening product that can be used at home or in private by the consumer and is safe and easy to use. A product for home use cannot utilize the compositions or products for whitening teeth that are available for use by a trained dental professional. For example, the 30% hydrogen peroxide bleaching agent utilized by many dental practitioners to bleach teeth is sufficiently concentrated to be irritating and potentially dangerous for home use by the consumer.

There are available in the marketplace dentifrice compositions for home use which contain 1–3% by weight concentrations of hydrogen peroxide and when applied on the teeth using a mouth guard or tray, effect whitening of stains. However, these compositions are considered to have slow bleaching effect.

Illustrative of oral compositions containing peroxide compounds include U.S. Pat. No. 4,988,450; U.S. Pat. No. 4,980,152, U.S. Pat. No. 4,839,156, U.S. Pat. No. 4,522,805, U.S. Pat. No. 4,567,036, U.S. Pat. No. 4,405,599 and U.S. Pat. No. 3,657,417.

U.S. Pat. No. 4,988,450 and U.S. Pat. No. 3,657,417 disclose formulating oxygen liberating compositions for the whitening of teeth utilizing anhydrous powders or water-free pastes or gels.

U.S. Pat No. 4,980,152 discloses an aqueous oral gel composition comprising about 0.5 to about 10% by weight urea peroxide and 0.01 to 2% by weight of a fluoride providing compound. The composition further includes a thickening agent such as carboxy polymethylene, a non-ionic surfactant such as Pluronic F127, alkali soluble cellulose ethers as viscosity increasing agents, potassium phosphate as a buffering agent and glycerine as a carrier and flavoring and sweetening agents.

U.S. Pat. No. 4,839,156 discloses a water containing hydrogen peroxide-Pluronic thickener oral gel composition. The composition, although effective at bleaching teeth and avoiding tissue damage, exhibits relatively slow whitening action.

U.S. Pat. Nos. 4,522,805 and 4,567,036 disclose a stable toothpaste for controlling periodontal disease, containing an oxidizing agent such as urea peroxide in a paste carrier comprising an anionic detergent, sorbitol and glycerin humectant and a thickening agent.

U.S. Pat. No. 4,405,599 discloses a toothpaste consisting essentially of a combination of calcium peroxide and sodium perborate oxidizing agents, dicalcium phosphate, calcium carbonate and magnesium carbonate cleaning agents, sorbitol humectant, cornstarch and cellulose gum thickening agents, and an anionic detergent.

U.S. Pat. No. 3,988,433 discloses oral compositions containing specific organic peroxyacids which remove stain from teeth. The specific peroxyacids disclosed are aryl peroxyacids and alkyl diperoxy acids having alkylene groups containing 5–11 carbon atoms. The patentee teaches that it is surprising that these specific organic peroxyacids are effective against stain as most other organic peroxyacids are relatively ineffective except when used at elevated temperatures and/or for long exposure times.

European Patent Application 0 400 858 discloses a denture cleaning composition comprising an inorganic persalt bleaching agent, an organic peroxy bleach precursor and an effervescence generator.

SUMMARY OF THE INVENTION

In accordance with the present invention, it has now been unexpectedly found that oral compositions which include peroxyacetic acid exhibit heightened whitening of teeth and stain removal when applied to teeth at ambient or oral temperatures.

As will hereinafter be illustrated, the oral compositions of the present invention exhibit better whitening of teeth than attained by prior art bleaching compounds.

Peroxyacetic acid is known to the art as a bleaching agent for fabrics, e.g., U.S. Pat. No. 3,852,210, U.S. Pat. No. 4,444,674 and U.S. Pat. No. 4,536,314.

French Patent 2,187,288 teaches the use of peroxyacetic acid in combination with an amine compound in oral compositions as an anti-caries and anti-plaque agent. However, as will hereinafter be demonstrated, the amount of peroxyacetic acid present in the disclosed composition (i.e., 0.008 moles/liter or 0.06% by weight) when used in combination with the amine and other specified ingredients is not effective in whitening teeth.

It is within the scope of the present invention that peroxy acetic acid may be used directly (as by swab application), incorporated in an oral composition such as a toothpaste, gel or rinse that is to be applied topically, or generated in situ in the oral composition by the reaction of a peroxide source such as hydrogen peroxide, urea peroxide, sodium perborate, sodium percarbonate, and all metal peroxides, for example, $SrO_2$, $CaO_2$ and $NaO_2$ with a peroxyacid precursor or activator containing labile acetyl groups. Illustrative examples of such activators include tetracetylethylene diamine, pentaacetyl glucose, tetracetyl glycol uril, sorbitol hexaacetate or fructose pentaacetate.

The amount of peroxyacetic acid incorporated in the oral composition will vary dependent upon its intended use. For use by trained professionals in office treatments, the concentration of peroxyacetic acid incorporated in the oral composition can vary from about 0.25% to about 5% by weight.

To effect in situ generation of peroxyacetic acid in the oral composition, the peroxide source is present in the composition at a concentration about 0.5 to about 30% by weight, preferably about 1.5 to about 10% by weight, and the activator is present in the composition in an amount sufficient to completely react with the peroxide source, e.g. about 0.1 to about 30 percent by weight and preferably about 1.5 to about 10% by weight.

For professional use, oral compositions containing peroxyacetic acid may be prepared by the dentist in his office from concentrated peroxyacetic acid solutions, for example, 40% peroxyacetic acid solution may be diluted with water to a final concentration of 1%. This solution can then be gelled using fumed silica, and applied to the patient's teeth by the dentist, or applied directly by the dentist without further adjuvants.

For home use, such high concentration of peroxyacetic acid cannot be used safely by the typical consumer and therefore the useful range of peroxyacetic acid in the oral composition is between 0.01 to 0.50% by weight. The preferred range in a rinse is between about 0.05% to about 0.1% by weight and the preferred concentration in a gel or paste is 0.25% by weight.

Peroxyacetic acid-containing oral compositions are conveniently prepared as a rinse, gel or paste to provide a safe and easy form in which it may be applied topically to the user's teeth. Mouthrinse compositions which have been found useful for the practice of the present invention generally comprise water, such as deionized water as the vehicle and, optionally, other ingredients such as non-toxic alcohols such as ethanol, flavors, stabilizing agents, sweeteners, and humectants such as glycerine and sorbitol.

Gels or pastes formulated to contain peroxyacetic acid as the whitening agent also include a gelling agent such as a polyoxyethylene polyoxypropylene block copolymer, a humectant such as glycerine, sorbitol, a polyethylene glycol, a nonionic surfactant, sweetener and flavor, the gel or paste having a pH of about 4.0 to 6.0. Water is present in the gel or paste and constitutes about 40–70% by weight of the oral composition. Distilled or deionized water is preferred to prevent minimal contamination.

Polyoxyethylene polyoxypropylene block copolymers which are nonionic and useful gelling agents in the oral compositions of the present invention are represented by the formula $$HO(C_2H_4O)_b(C_3H_6O)_a(C_2H_4O)_bH$$

wherein a is an integer such that the hydrophobic base represented by $(C_3H_6O)$ has a molecular weight of about 2750 to 4000, b is an integer such that the hydrophilic portion (moiety) represented by $(C_2H_4O)$ constitutes about 70–80% by weight of the copolymer. Pluronic Polyols of the F (soild flake or powder) type are preferred. Examples of such Pluronic compounds are Pluronic F88, F98, F108 and F127. The most preferred gelling agent is Pluronic F127, which has a molecular weight of 4000 and contains 70% of the hydrophilic polyoxyethylene moiety.

Other useful thickening agents include colloidal carboxyvinyl polymers such as those sold under the trademark Carbopol 934 and 940, cross-linked polycarboxylate polymers available from GAF under the designation Gantrez ACV-4006 or stabilizer 06, polyvinyl pyrrolidone, and fumed silica available from Cabot, Inc. under the trademark Cab-O-Sil.

The gelling agent is present in the oral composition of the present invention at a concentration of about 10 to about 40% by weight and preferably about 15 to about 30% by weight of the composition.

Illustrative of the polyethylene glycols useful in the practice of the present invention include polyethylene glycols known by the trademark CARBOWAX which are nonionic polymers of ethylene oxide having the general formula:

$$HOCH_2(CH_2OCH_2)_nCH_2OH$$

wherein n represents the average number of oxyethylene groups. The Carbowax polyethylene glycols are designated by a number such as 400, 600, 800, etc. which represents the average molecular weight. The average molecular weight of the polyethylene glycols used herein is about 200–1000, preferably 400–800 and most preferably 600.

Other useful humectants include non-hydroxylated compositions such as capped polyethylene glycol, where the hydrogens on the hydroxyl groups have been replaced with methyl groups. Humectants such as glycerine, sorbitol polyethylene glycol and capped polyethylene glycols are included in the oral composition of the present invention at a concentration of about 10 to about 40% by weight and preferably about 15 to about 25% by weight of the composition.

Nonionic surfactants are included in the oral compositions of the present invention and serve as a solubilizing and emulsifying agent. A particularly useful nonionic surfactant is a water soluble polyoxyethylene monoester of sorbitol with a $C_{10-18}$ fatty acid ester of sorbitol (and sorbitol anhydrides), consisting predominantly of the monoester, condensed with about 10–30, preferably about 20, moles of ethyleneoxide. The fatty acid (aliphatic hydrocarbon-monocarboxylic acid) may be saturated or unsaturated, e.g. lauric, palmitic, stearic, oleic acids. Tween 20 is especially preferred, which is a polyoxyethylene (20) sorbitan monolaurate. Capped polyalkylene oxide copolymer nonionic surfactants in which the hydrogens on the hydroxyl groups have been replaced with methyl groups are also useful in the present invention. These types of surfactants are described in U.S. Pat. No. 4,988,452 and U.S. Pat. No. 4,877,544.

The nonionic surfactant constitutes about 0.5 to 5.0% by weight and preferably 0.5 to 3% by weight of the oral composition.

The flavor ingredient constitutes about 0.5 to 5.0% by weight of the oral composition of the present invention. Suitable flavoring constituents are flavoring oils, e.g., oils of spearmint, peppermint, wintergreen, sassafras, clove, sage, eucalyptus, marjoram, cinnamon, and methyl salicylate, ethyl acetate and menthol.

A sweetening material is preferably also employed as a complement to the flavoring material. Suitable sweetening agents are water soluble and include sodium saccharin, sodium cyclamate, xylitol, aspartame and the like, in concentrations of about 0.10 to 1.0% by weight. Sodium saccharine is preferred.

Pyrophosphate salts having anti-tartar efficacy such as a dialkali or tetra-alkali metal pyrophosphate salts such as $Na_4P_2O_7$, $K_4P_2O_7$, $Na_2H_2P_2O_7$ and $K_2H_2P_2O_7$, long chain polyphosphates such as sodium hexametaphosphate and cyclic phosphates such as sodium trimetaphosphate are incorporated in the oral compositions of the present invention preferably at a concentration of about 0.5 to about 8.0% by weight.

Peroxide stabilizers such as sequestering agents, buffers, acidulating agents, coating or encapsulating agents may also be included in the oral compositions of the present invention. Examples of suitable sequestering agents are salts of ethylene diamine tetraacetic acid, diethylene triamine pentaacetic acid, phosphonates such as Dequest (trademark) available from Monsanto Chemical Company and azacycloheptane 2', 2' diphosphonate. Such agents stabilize the peroxide containing compositions by chelating metal ions such as $Fe^{+3}$, $Mn^{+2}$ and $Cu^{+2}$. The agents may be incorporated in the compositions of the present invention at a concentration of about 0.1 to about 6.0% by weight of the composition.

Soluble and insoluble calcium compounds may also be added to the composition, like calcium acetate, dicalcium phosphate dihydrate, and calcium pyrophosphate and combinations thereof. These compounds provide soluble calcium and minimize the amount of mineral loss from teeth after exposure to compositions useful in this invention.

The calcium compounds are included in the oral compositions of the present invention at a concentration of about 1 to about 40% by weight and preferably about 5 to about 20% by weight.

The oral composition of the present invention may be prepared by suitable mixing of the ingredients. For instance, to prepare a gel or paste, the peroxyacetic acid, a gelling agent such as Pluronic F127 and humectant and sweetener are mixed using a Ross mixer, under vacuum for about 30 minutes. The peroxyacetic acid is then added, followed by the nonionic surfactant and flavor. The ingredients are then mixed under vacuum for an additional 15-30 minutes. The resulting gel or cream is then tubed.

In home use, approximately 1 gram of the gel or cream is applied to a toothbrush and brushed vigorously onto the teeth. Brushing is continued for 1-3 minutes. The gel or paste is allowed to remain on the teeth for as long as possible.

Also in accordance with present invention, an aqueous solution of the peroxyacetic acid may be applied as an office procedure by dental professionals, alone or with the addition of suitable adjuvants.

In accordance with the present invention, the whitening composition may be used on a daily basis with a noticeable whitening of the user's teeth within a short period of time following regular use.

The following examples are further illustrative of the present invention, but it is understood that the invention is not limited thereto. All amounts and proportions referred to herein and in the appended claims are by weight unless otherwise indicated.

EXAMPLE I

A Minolta CR-221 Chroma Meter was used to measure the optical properties of extracted upper central human incisors before and after the application of bleaching agents. The teeth selected for the test matched each other as closely as possible as determined by using the Chroma Meter. The measurement technique involved wrapping the teeth tightly with a thin, optically clear plastic wrapping material before placing them in the aperture of the meter for measurement. The 3 mm diameter circular aperture measured the optical properties of the central part of the anterior surface of each tooth.

The Chroma Meter provides values of the optical parameters $L^*$, and $b^*$ in the CIE system of color measurement. $L^*$ relates to the overall grey-scale lightness or darkness of a material, and $b^*$ to its yellowness or blueness. Other factors being equal, it is preferred to have high values of $L^*$ (indicating optical lightness) and low or even negative values of $b^*$, indicating the absence of yellowness, a highly obvious and undesirable optical characteristic of teeth.

The teeth to be bleached had been stored under refrigeration in water since extraction. The bleaching treatment involved placing each tooth in a sealed vial with 15 ml of the bleaching solution and incubating at 39° C. (the approximate temperature of a human mouth) for an interval of 2 hours. For tooth "A", the bleaching solution was a 1% aqueous solution of peroxyacetic acid, and for tooth "B" the bleaching solution comprised a 30% aqueous solution of hydrogen peroxide. Both solutions were adjusted to pH 4.0 with sodium hydroxide. At intervals, the teeth were removed from the vials for optical measurements, then replaced. Initially, both teeth essentially matched Dentsply Trubyte ™ Color-Ordered Shade Guide B67 in appearance.

Table I summarizes the response of each tooth to the treatment:

TABLE I

| Time, minutes | Tooth "A" (1% peroxyacetic acid) | | Tooth "B" (30% hydrogen peroxide) | |
|---|---|---|---|---|
| | L* | b* | L* | b* |
| 0 | 45.2 | 6.5 | 48.1 | 4.8 |
| 60 | 49.5 | 1.4 | 49.1 | 3.6 |
| 90 | 48.4 | −1.1 | 47.1 | 3.2 |
| 120 | 51.2 | −2.8 | 48.6 | 2.4 |

Reference to the data recorded in Table I indicates that Tooth "A" was much superior to tooth "B" in final appearance (6 Shade Guide units difference between B53 and B55) and, as the instrument indicated, was substantially lighter and less yellow. The difference is all the more remarkable considering that the peroxyacetic acid had a concentration of only 1% as compared with the 30% concentration of the hydrogen peroxide. At the end of the bleaching period, both teeth had retained a glossy appearance.

EXAMPLE II

A gel was prepared using the following ingredients:

| INGREDIENTS | % Wt. |
|---|---|
| Polyethylene glycol 600 | 15.0 |
| Peroxy acetic acid (35% solution) | 0.394 |
| Pluronic F-127 | 20.0 |
| Flavor | 1.5 |
| Tween 20 | 1.2 |
| Saccharin | 0.2 |
| Deionized $H_2O$ q.s. to | 100 |

The gel was prepared by admixing the Pluronic F127, PEG-600 and sweetener using a Ross mixer, under vacuum for about 30 minutes. The peroxyacetic acid was then added, followed by the Tween 20 and flavor. The ingredients are then mixed under vacuum for an additional 15-30 minutes. The resulting gel or cream was then tubed.

To test the whitening efficacy of the gel, bovine teeth were stained with a staining broth consisting of coffee, tea, mucin, microbiological media, and a chromogenic microorganism. Stained bovine teeth selected for the test showed the same amount of discoloration. To test the whitening efficacy of the gel, the teeth were immersed in 5 grams of the gel at 37° C. Before immersion, the color of the teeth was measured with a Gardner colorimeter in which $L^*$ is a measure of response to the eye to lightness and darkness, and b is a measure of yellowness. The higher the $L^*$ value and the lower $b^*$ value, the whiter teeth appear.

The whiteness index was calculated using the following equation:

$$Delta\ E = [(Delta\ L^*)^2 + (Delta\ b^*)^2]^{\frac{1}{2}}$$

The teeth remained immersed in the gel for 15 hours. The whitening index (Delta E) of the immersed teeth are summarized in Table I below.

For purposes of comparison, the procedure of Example I was repeated with exception that the teeth were immersed in a commercial rinse formulation containing 1.5% hydrogen peroxide designated composition "C". The color measurements of comparative composition C are also summarized in Table II below.

TABLE II

| COMPOSITION | $L^*/b^*$ at indicated time (hours) | | Delta E |
|---|---|---|---|
| | 0 hr | 15 hr | |
| Ex. II | 31.9/16.0 | 54.8/6.6 | 24.8 |
| Ex. II | 28.7/17.9 | 57.3/7.8 | 30.3 |
| Ex. II | 35.8/17.6 | 57.1/9.4 | 22.8 |
| C | 38.2/17.4 | 50.1/14.5 | 12.2 |
| C | 35.5/13.9 | 52.0/11.7 | 16.6 |
| C | 31.1/18.2 | 48.8/15.9 | 17.8 |

The data in Table I indicates that the composition of Ex. II is on average 68% more effective in bleaching dental stains. Also there is a marked decrease in the $b^*$, i.e. yellowness, for the teeth exposed to peroxyacetic acid when compared to those exposed to the hydrogen peroxide composition.

EXAMPLE III

The procedure of Example II was repeated with the exception that aqueous solutions containing 0.05% and 0.1% by weight peroxyacetic acid were substituted for the gel composition of Example II.

To test the bleaching efficacy of the peroxyacetic acid, extracted human molars which had been refrigerated and kept wet were selected which showed more than the usual discoloration. The molars were immersed in 15 ml of the solutions at room temperature. The Delta E values of the immersed teeth are summarized in Table III below.

TABLE III

| TOOTH | PEROXYACETIC ACID (%) | Delta E values at indicated time (hours) | | | |
|---|---|---|---|---|---|
| | | 0 hr | 6.5 hrs. | 48 hrs. | 96 hrs. |
| 1 | 0.05 | 0.0 | 6.0 | — | 13.5 |
| 2 | 0.10 | 0.0 | — | 4.9 | — |

The Delta E values listed in Table III indicate that peroxyacetic acid is effective as a whitening agent at relatively low concentrations, that is, 0.05% by weight.

EXAMPLE IV

The procedure of Example III was repeated except that in a series of runs, the teeth were placed in 15 ml of 1% by weight peroxyacetic acid solution and kept in a sealed vial in an incubator set at 25° C. and 39° and incubated for 15-60 minutes.

The tooth samples were selected which showed more than usual discoloration equivalent to Munsell values no greater than 7.05 as estimated from comparison with Dentsply Trubyte Bioform Color Ordered Shade Guide artificial teeth samples. The Guide is supplied with a chart showing the Munsell hue, value, and chroma for each sample. The Guide contains a set of 24 artificial teeth ranging from Munsell values of 6.55 (most discolored) to 7.80 (desired whiteness).

The Munsell values of the teeth immersed in 1% by weight peroxyacetic acid at 25° C. and 39° C. are summarized in Tables IV and V below.

For purposes of comparison, the procedure of Example III was repeated with the exception that 30% hydrogen peroxide solution, designated Composition "$C_1$", or 10 grams/liter (available chlorine) sodium hypochlorite designated Composition "$C_2$" or 20 g/l (available chlorine) sodium hypochlorite designated Composition "$C_3$" was substituted for the 1% peroxyacetic acid. The Munsell values of these comparative bleaching agents are also summarized in Tables IV and V below.

TABLE IV

| | EXPOSURE AT 25° TIME (MINUTES) MUNSELL VALUES | | | | |
|---|---|---|---|---|---|
| COMPOSITION | 0 | 15 | 30 | 45 | 60 |
| Ex. IV | 7.05 | 7.45 | 7.45 | 7.45 | 7.80 |
| $C_1$ | 6.65 | 6.80 | 7.0 | 7.05 | 7.05 |

TABLE V

| COMPOSITION NO. | EXPOSURE AT 39° C. Time (Minutes) Munsell Values | | | | | |
|---|---|---|---|---|---|---|
| | 0 | 15 | 30 | 45 | 60 | 90 |
| Ex. IV | 7.05 | 7.30 | — | 7.45 | 7.80 | — |
| $C_1$ | 6.65 | 7.00 | 7.20 | 7.20 | 7.20 | — |
| $C_2$ | 7.15 | 7.15 | 7.15 | 7.15 | — | 7.30 |
| $C_3$ | 7.15 | 7.30 | 7.30 | 7.30 | — | 7.45 |

The data recorded in Tables IV and V indicate that although 1% by weight peroxyacetic acid, 30% hydrogen peroxide and 10–20 g/1 sodium hypochlorite all showed higher Munsell values, peroxyacetic acid was superior to both hydrogen peroxide and sodium hypochlorite in whitening teeth.

EXAMPLE V

The procedure of Example III was repeated using a solution of 1% by weight peroxyacetic acid heated to 37° C.

A comparative composition, designated Composition "$C_4$", which was a solution disclosed in French Patent Number 2,187,288 containing the following ingredients:

| | % by Weight |
|---|---|
| $CH_3COOOH$ | 0.008 |
| Glycine | 0.05 |
| NaCl | 0.05 |
| NaOH | 0.05 | was evaluated as a whitening composition. Water was used as a control.

The Delta E (increase in whiteness) measurements after 9 hours of immersion in the test solutions are recorded in Table VI below.

TABLE VI

| COMPOSITION NO. | EXPOSURE AT 37° C. Delta E |
|---|---|
| Ex. III | 6.8 |
| $C_4$ | 0.0 |
| $H_2O$ | 0.0 |

EXAMPLE VI

One gram of purified tetraacetyl ethylenediamine (TAED) was dissolved in 46 grams of N-methylpyrrolidinone (NMP). Separately, a saturated solution of sodium monoperborate in 4 milliliters of water was prepared. The two solutions were mixed, and 15 milliliters of the resulting mixture were added to each of two small screw-capped vials. To each vial was added a discolored human tooth. One vial was placed in an incubator at 39° C., and the other vial was kept at room temperature. After 4.5 hours, both teeth were bleached to a degree approximating Shade Guide B59, the lightest shade in the series, with slight reddish tinge to the tooth which had been stored at room temperature. The teeth were then replaced in their respective vials at their respective temperatures until a total time of 24 hours elapsed, whereupon both had been bleached to a shade whiter than B59. The tooth which was stored at 39° C. was much whiter than B59, while the tooth stored at room temperature, although whiter than B59, still had a slight reddish tinge.

EXAMPLE VII 0.500 grams of recrystallized TAED was dissolved in 50 grams of NMP (Solution 1) and 0.877 grams of sodium monoperborate was dissolved in 33.3 grams of water (Solution 2) to prepare a one-phase composition. Both solutions were warmed to about 39° C. Solution 2 was poured into Solution 1, whereupon a further warming effect was noted. Some cloudiness was noted when the solutions were mixed, but there was no gross phase separation. The mixed solution was cooled to about 38° C. A discolored human cuspid which approximately matched Shade Guide B94 was placed in a warmed vial, and to it was added about 15 ml of the warm mixed solution. The capped vial was placed in an incubator at 39° C. After 15 minutes, the tooth had been bleached to a color approximating Shade Guide B53 (eight shades improvement over original).

What is claimed is:

1. A method of whitening stained or discolored teeth which comprises applying to said teeth in the oral cavity an oral composition which in contact with teeth in the oral cavity will whiten stained or discolored teeth, the composition comprising a safe amount of peroxyacetic acid dissolved or suspended in a vehicle effective to whiten teeth in the oral cavity said vehicle having an acid pH, the amount of peroxyacetic acid being in the range of about 0.01 to about 5% by weight, and allowing the composition to remain on the teeth for a time sufficient to effect whitening thereof.

2. The method of claim 1, wherein the whitening composition is an aqueous solution containing peroxyacetic acid.

3. The method of claim 1, wherein the whitening composition is in the form of a gel.

4. The method of claim 1, wherein the peroxyacetic acid is present in the composition at a concentration of about 0.01 to about 5.0% by weight.

5. The method of claim 1 wherein the peroxyacetic acid is generated in situ by the incorporation in the composition of a peroxide source and a peroxy acid precursor.

6. The method of claim 5 wherein the peroxide source is sodium perborate.

7. The method of claim 5 wherein the peroxy acid precursor is tetraacetyl ethylenediamine.

8. The method of claim 5 wherein the peroxide source is present in the composition at a concentration of about 0.5 to about 30% by weight, and the peroxyacetic acid precursor is present in the composition at a concentration of about 0.1 to about 30 percent by weight.

* * * * *